United States Patent
Lange et al.

(10) Patent No.: US 6,468,658 B2
(45) Date of Patent: Oct. 22, 2002

(54) PROCESS FOR PREPARING GRIT BLASTING PARTICLES COATED WITH TITANIUM DIOXIDE

(75) Inventors: Gerlinde Lange, Langenselbold (DE); Manfred Schuck, Karlstein (DE); Katja Heck, Grosskrotzenburg (DE); Andreas Gutsch, Ranstadt (DE); Guido Zimmermann, Hanau (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/866,493

(22) Filed: May 29, 2001

(65) Prior Publication Data

US 2002/0032988 A1 Mar. 21, 2002

(30) Foreign Application Priority Data

Jun. 15, 2000 (DE) .......................................... 100 29 598

(51) Int. Cl.[7] .......................... B32B 15/02; B32B 27/02; B32B 17/02; B32B 5/16; B32B 19/00; B32B 9/00; B32B 21/02; B32B 23/02

(52) U.S. Cl. ........................ 428/404; 427/212; 427/215; 428/402

(58) Field of Search ................................ 427/212, 215, 427/216, 218, 223, 421, 424, 427; 428/351, 402, 404

(56) References Cited

U.S. PATENT DOCUMENTS 6,110,528 A * 8/2000 Kimura et al. ............... 427/215

FOREIGN PATENT DOCUMENTS

| DE | 298 21 398 U1 | 6/1999 |
| JP | 64-79001 | 3/1989 |

OTHER PUBLICATIONS

Copy of German Office Action in counterpart appln. No. 100 29 598.3, dated May 21, 2001.

* cited by examiner

Primary Examiner—Michael Barr
Assistant Examiner—Rebecca A. Blanton
(74) Attorney, Agent, or Firm—Smith, Gambrell & Russell, LLP

(57) ABSTRACT

A process for preparing grit blasting particles coated with titanium dioxide by sinter-fusing titanium dioxide on the surface of grit blasting particles made of a base material. A mixture of finely divided titanium dioxide and grit blasting particles is passed continuously through the flame in a flame reactor, with the aid of conveying air, wherein the titanium dioxide is sinter-fused on the surface of the grit blasting particles over an average residence time of 0.1 to 5 seconds in a temperature range from 600 to 1200° C. An increase in the adhesive bond between metal framework and a facing material made of plastics in dentures can be achieved when metal framework is grit blasted with a grit blasting agent containing titanium dioxide coated grit blasting particles and then the grit blasted and titanium dioxide coated surface is treated with a silane bonding agent.

20 Claims, 2 Drawing Sheets

PROCESS FOR PREPARING GRIT BLASTING PARTICLES COATED WITH TITANIUM DIOXIDE

INTRODUCTION AND BACKGROUND

The present invention relates to a process for preparing grit blasting particles coated with titanium dioxide by sinter-fusing titanium dioxide on the surface of grit blasting particles made of a base material.

Grit blasting particles coated with titanium dioxide are described in DE 298 21 398 and in Biomedizinische Technik, vol. 49, supplement 1, 35 (1995), and also a general process for preparing them. According to this, these types of titanium dioxide-coated particles are prepared by sinter-fusing an aqueous $TiO_2$ slip suspension on the material making up the particles. The particles are first intimately mixed with the $TiO_2$ slip suspension, the solvent is removed and then the slip which has dried onto the particles is sinter-fused at temperatures between 300 and 1400° C. These types of titanium dioxide-coated particles, preferably those made of inert corundum (aluminum oxide, $Al_2O_3$) as base material, are mainly used to grit blast, and simultaneously tribochemically coat with titanium dioxide, components for use in the human body and in particular in the oral cavity. When preparing components made from metallic materials for this type of use, such as in particular in dentistry when manufacturing frameworks made of dental alloys for dental repairs, grit blasting is a conventional working step for preparing the surface. Corundum is generally used as the grit blasting material in this case.

When manufacturing dentures, prosthetic metal frameworks such as crowns or bridges are coated with a tooth-coloured facing material in order to produce a more pleasing appearance. In particular in the case of removable dentures and long-term temporary products, plastic materials are preferably used as the facing material, rather than ceramics, due to their typical materials properties such as, for example, higher elasticity. Since the properties of the facing materials based on plastics clearly differ from those of the alloys from which the metal frameworks are manufactured, a permanent bond cannot be ensured without the use of adhesive bonding systems.

The extreme conditions in the oral medium cause problems, wherein the materials are subjected to moisture, temperature changes and mechanical strain as well as the individual's personal habits such as mode of eating and the taking of any medicaments. As a result of these effects, a peripheral gap often forms after a short time between the metal framework and the plastic facing. Discoloration occurs in this peripheral region due to the onset of metal corrosion and penetration by microorganisms. The different coefficients of thermal expansion of metal and plastics and the polymerization shrinkage of the latter, can produce certain stresses which, assisted by the formation of peripheral gaps and the effects of moisture and also mechanical strain, can lead to damage or even to loosening of the facing.

In principle, known processes for producing strong and as gap-free as possible composites of metal and plastics are substantially based on applying, in a first step, a siliceous layer to the metal surface which is then silanized in a second step by treatment with a silane bonding agent, for example a functional alkoxysilane. The silane acts as a chemical bonding agent between the silicatized metal surface and the polymeric facing material. The known processes differ substantially in the type and manner of application of the silicate layer. In DE 38 02 043 this is produced by tribochemical coating when grit blasting the metal surface using silicon dioxide-coated corundum as the blasting grit. A process of this type is used in dentistry under the name "Rocatec".

From the literature references mentioned at the beginning, it can be seen that tribochemical coating with titanium dioxide has better biocompatibility than siliceous coatings and in combination with a silane bonding agent, due to higher resistance to hydrolysis, leads to a much better adhesive bond between metal and plastic facing.

However, in practice it has been shown that the preparation of this type of titanium dioxide-coated grit blasting particles by sinter-fusing an aqueous $TiO_2$ slip suspension on the particle material does not lead to a sufficiently uniform product. This contains, in particular, particles with varying amounts, thickness and distribution of the $TiO_2$ coating and also free $TiO_2$ particles with a high proportion of fines. This has a disadvantageous effect on anchoring the $TiO_2$ layer in and on the metal surface during the working process of grit blasting and tribochemical coating, wherein in particular the virtually unavoidable proportion of very fine $TiO_2$ particles impairs the resulting metal/plastic adhesive bond.

An object of the present invention therefore is to find and develop a process for preparing grit blasting particles coated with titanium dioxide which does not have the disadvantages described above.

SUMMARY OF THE INVENTION

Surprisingly, it has now been found that, in particular for long-term use, substantially better metal/plastic adhesive bond values can be produced if the grit blasting particles used for blasting and at the same time tribochemically coating with titanium dioxide metallic components have been obtained by sinter-fusing titanium dioxide on the grit blasting particles. According to the invention, the coating procedure is performed in such a way that a mixture of finely divided titanium dioxide and grit blasting particles are continuously passed through the flame in a flame reactor, with the aid of conveying air, and the titanium dioxide is sinter-fused on the surface of the grit blasting particles over an average residence time of 0.1 to 5 seconds in a temperature range from 600 to 1200° C.

Thus, the invention provides a process for preparing grit blasting particles coated with titanium dioxide by sinter-fusing titanium dioxide on the surface of the grit blasting particles made of a base material which is characterized in that a mixture of finely divided titanium dioxide and grit blasting particles is passed continuously through the flame of a flame reactor, with the aid of conveying air, wherein the titanium dioxide is sinter-fused on the surface of the grit blasting particles over a residence time of 0.1 to 5 seconds in a temperature range from 600 to 1200° C.

The core feature of the process according to the invention is that a dry powder mixture is reacted in a flame reactor, wherein the titanium dioxide is sinter-fused on the grit blasting particles by the direct effect of heat in a flame.

BRIEF DESCRIPTION OF THE DRAWINGS

The present invention will be further understood with reference to the accompanying drawings, wherein.

DETAILED DESCRIPTION OF THE INVENTION

First of all a homogeneous mixture of finely divided titanium dioxide and grit blasting particles is produced. Conventional mixing procedures and equipment, for example a plough bar mixer, may be used for dry mixing the powders.

The mixture is then passed into a flame reactor at a metered rate of delivery in accordance with the objective. A gravimetric metering screw, for example, is suitable for this purpose.

There, the powder mixture is passed continuously through the flame in the flame reactor, using conveying air. The titanium dioxide is sinter-fused on the surface of the grit blasting particles over an average residence time of 0.1 to 5 seconds within a temperature range from 600 to 1200° C. The flame is expediently operated using fuel gas and air.

The mixture is preferably blown centrally, with the aid of conveying air, at a rate of 1 to 50 m/s into a ring flame operated with fuel gas.

The sintered product is then separated from the fuel gas stream, for example with a hot gas filter, and collected.

As the last step, this may be followed by sieving and dedusting the blasting grit obtained, which is coated with $TiO_2$ obtained.

Figure 1:
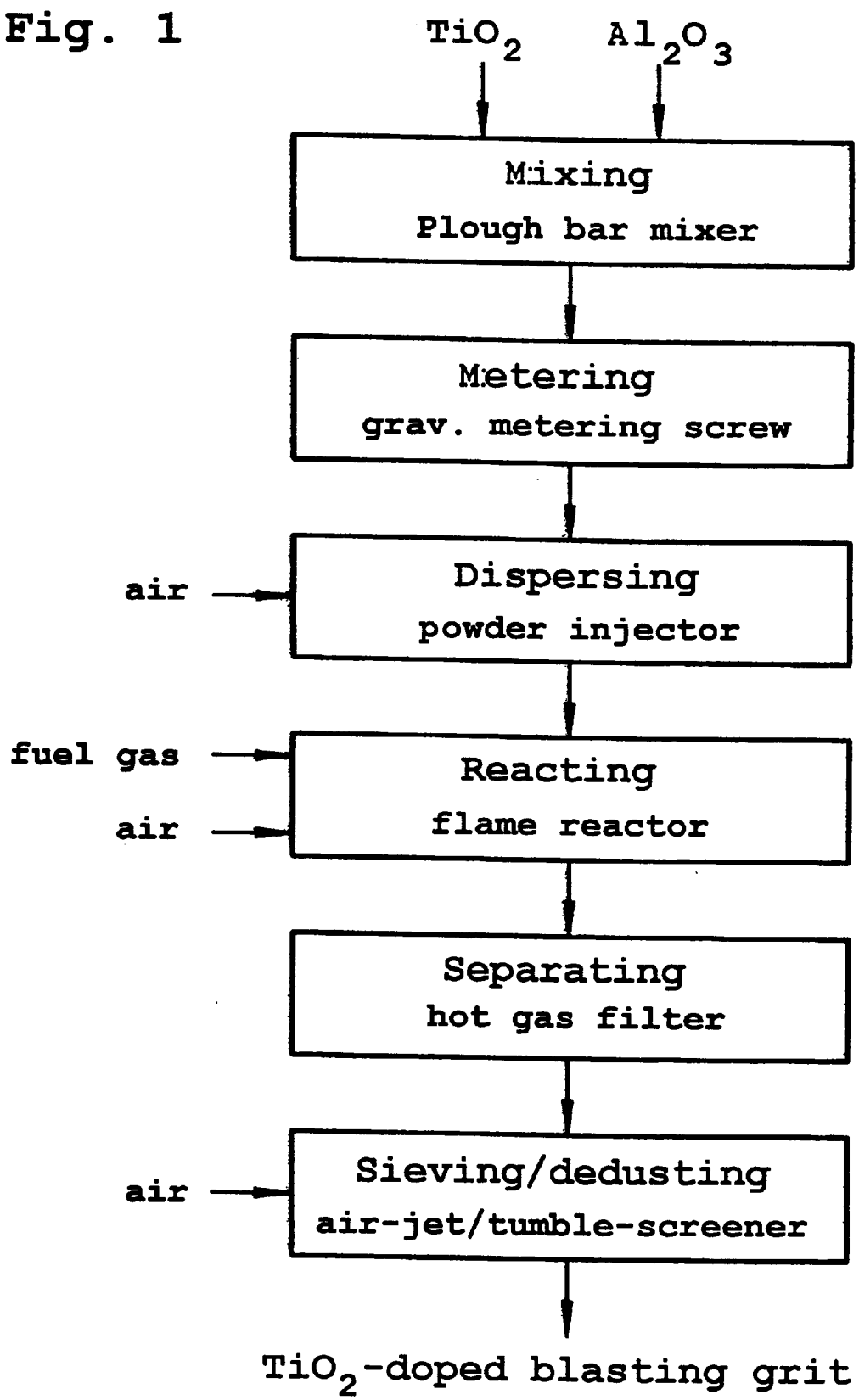
FIG. 1 shows, in a schematic form, a flow diagram of the main procedures in the process of the invention using the example of coating corundum blasting grit with $TiO_2$.
Figure 2:
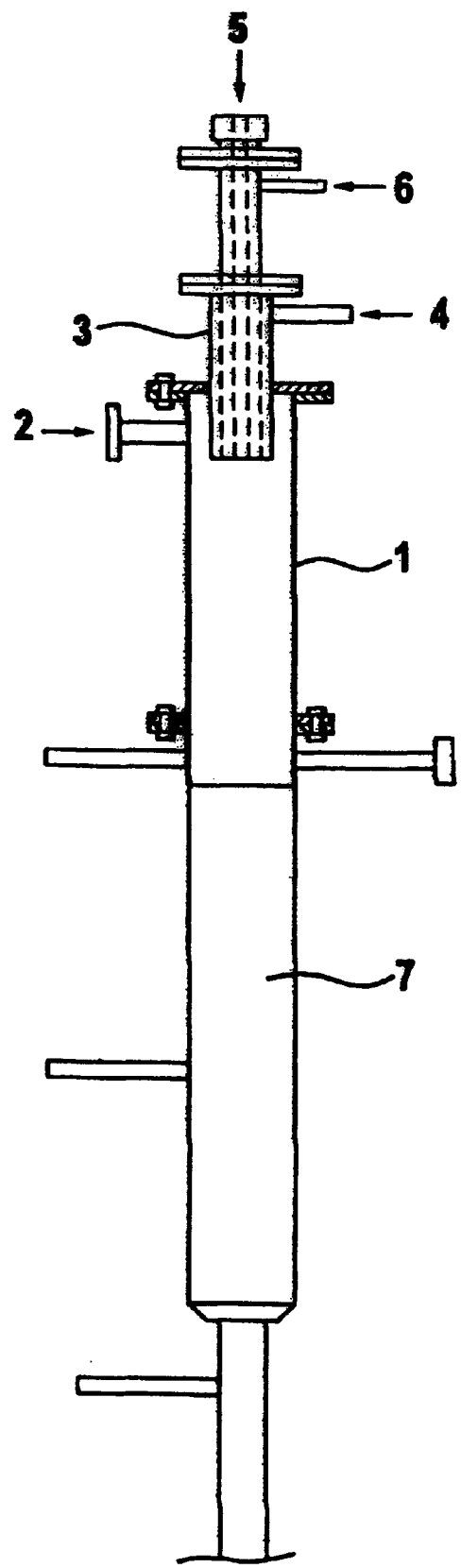
FIG. 2 shows, by way of example and in a schematic manner, the main structure of a flame reactor which is suitable for performing the process according to the invention.

The reactor shown in FIG. 2 is a tubular reactor. The flame reactor consists of a combustion chamber (1) with an air supply (2), a burner lance (3) with fuel gas supply (4), powder injector (5), provision for flushing out with nitrogen (6) and a reaction tube (7). The fuel gas is introduced into the combustion chamber (1) via the annular gap in the burner lance (3). The combustion air (2) is introduced tangentially into the combustion chamber (1).

Ignition takes place at the mouth of the burner lance, wherein a laminar diffusion flame is produced which is designed as a ring flame. The powder mixture is dispersed in the fuel gas flame in the combustion chamber (1) of the flame reactor via the powder injector (5) operated with compressed air, with the aid of, for example, a gravimetric metering screw. The powder is supplied centrally in the flame via the powder injector (5) designed as a central tube. A second flame front is formed in the feed zone, due to the conveying air. The titanium dioxide is thermally fixed and sinter-fused on the aluminum oxide particles during the residence time in the flame and in the reaction tube (7).

Typical process parameters for practical performance of the sintering procedure in the flame reactor are, for example:

| | |
|---|---|
| Throughput: | 0.1–100 kg/h (powder mixture) |
| Temperature: | 600–1200° C. |
| Volume flow: | 1–20 m³N/h (hydrogen) |
| | 5–100 m³N/h (secondary air) |
| | 0.5–10 m³N/h (dispersion air) |
| Residence time: | 0.1–5 seconds |

The grit blasting particles are separated from the waste gas stream, for example with a metal filter tube, at 300–550° C., collected in containers and allowed to cool.

The blasting grit coated with $TiO_2$ is expediently sieved to a particle size of less than 500 μm, for example with a air-jet tumble-screener. The removal of oversized titanium dioxide may take place using the sizing air.

Blasting grit made of any base material may be coated with titanium dioxide using the process according to the invention. The grit blasting particles preferably consist of a ceramic material, glass or metal as base material. Grit blasting particles which consist of aluminum oxide as base material are particularly preferred. Such materials are well known in the art.

The shape and size of the grit blasting particles is largely non-critical. The particles may be substantially spherical or have an irregular, angular or rough-edged shape. The diameter of the grit blasting particles is in the range 1 μm to 500 μm and preferably in the range 20 μm to 250 μm.

The titanium dioxide used for coating is of commercial quality and may have particle sizes in the range 0.001 μm to 10 μm, preferably in the range 0.01 μm to 0.1 μm.

The surface covering of titanium dioxide on the particles preferably covers the entire surface, but may also be a partial covering. This can easily be adjusted by adjusting the ratio by weight of grit blasting particles to titanium dioxide. A mixture of 0.1 to 30 wt.%, preferably 1 to 5 wt.%, of titanium dioxide and 70 to 99.9 wt.%, preferably 95 to 99 wt.% of grit blasting particles is expediently used.

Grit blasting particles coated with titanium dioxide prepared according to the invention are very advantageously used for grit blasting and simultaneously tribochemically coating components with titanium dioxide for use in the human body and in particular in the oral cavity.

These types of components for use in the human body and in the oral cavity may consist of metallic, ceramic, metal-ceramic or composite materials.

Tribochemical coating with titanium dioxide is advantageous in particular in the case of dental repairs and for implants made of metallic materials. $TiO_2$ coatings, as compared with other materials or material surfaces, exhibit particularly pronounced biocompatibility.

The use of particles coated with $TiO_2$ according to the invention as grit blasting agents in the dental engineering manufacture of dentures faced with plastics is particularly advantageous. Here, the metal framework is blasted in a manner known per se using a blasting grit consisting of particles coated with titanium dioxide according to the invention, then the grit blasted, and thus tribochemically coated with $TiO_2$, surface is treated with a silane bonding agent conventionally used in dental engineering and then the plastics facing is applied in a conventional manner.

Surprisingly, it has been shown that, in comparison with other methods or bonding systems, in particular the method based on $TiO_2$ in accordance with DE 298 21 398 but also the "Rocatec" process based on silicate, an unexpected increase in the adhesive bond between metal framework and facing material made of plastics is noted in dentures. This is demonstrated particularly clearly and in a manner relevant to normal practice in long-term trials with regard to temperature changes and the effects of moisture under conditions prevailing in the body.

To test the adhesive bond between metal and plastics, a test method based on the method in ISO 10 477 was used.

Cast metallic dental test items (dimensions: l=20±1 mm, b=10±1 mm, d=2±0.5 mm) made of commercially available dental alloys were uniformly grit blasted with corundum (particle size about 110 μm) in grit blasting equipment normally used for dental engineering, using a nozzle with a diameter of 0.85 mm and a pressure of 2 bar for 20 s. Then the test items were grit blasted with $TiO_2$ coated blasting grit at a pressure of 3 bar, but otherwise under identical conditions, followed by suction treatment. The coated area was about 1 cm² in the middle of the samples. Loosely adhering particles were removed from the coated area with a dry brush, then the silane was applied and allowed to evaporate for 2 minutes. Then the opaque material, a commercially available polymeric facing material, was applied in two layers and each layer was polymerized. The dentine was applied to the platelets with the aid of a conical steel mould (diameter d=5 mm, depth h=2.3 mm) and polymerized in the mould. Then the sample was removed from the mould and post heat-treated in commercially available polymerisation equipment.

Five samples were each sheared off without being subjected to further strain and a further 5 samples were each subjected to 30000, 70000 and 110000 temperature changes in water (5° C./55° C.; immersion time 30 seconds each time), wherein 5 samples were also each tested, after 110000 changes, after 12 months storage in water at 37° C.

To determine the shear strength, the facing plastic was sheared off parallel to the metal surface using a universal test machine with a feed rate of 1 mm/min. The results are shown in tables 1 to 4 below.

TABLE 1

Alloy: Degunorm ® (high gold content noble metal alloy)
Facing plastic: CompoPlus ® (acrylate-based)

| | Shear strength (MPa) | | | | |
|---|---|---|---|---|---|
| Example | initial | 30000 TC | 70000 TC | 110000 TC | 110000 TC 12 months storage in water |
| Rocatec (tribo-chemical silicate) | 15.1 | 11.9 | 9.3 | 8.8 | 8.6 |
| DE 298 21 398 (tribo-chemical TiO₂) | 16.5 | 15.7 | 14.6 | 11.5 | 10.4 |
| Invention | 12.8 | 16.1 | 13.4 | 13.0 | 12.5 |

TABLE 2

Alloy: Degupal ® G (palladium-based alloy)
Facing plastic: CompoPlus ® (acrylate based)

| | Shear strength (MPa) | | | | |
|---|---|---|---|---|---|
| Example | initial | 30000 TC | 70000 TC | 110000 TC | 110000 TC 12 months water at 37° C. |
| Rocatec (tribo-chemical Silicate) | 11.9 | 11.4 | 7.4 | 7.1 | 6.9 |
| DE 29 821 398 (tribo-chemical TiO₂) | 17.2 | 11.1 | 8.3 | 5.5 | 5.3 |
| Invention | 13.9 | 13.7 | 12.6 | 11.5 | 10.8 |

TABLE 3

Alloy: Pallatop ® (palladium/gold alloy)
Facing plastic: CompoPlus ® (acrylate-based)

| | Shear strength (MPa) | | | | |
|---|---|---|---|---|---|
| Example | initial | 30000 TC | 70000 TC | 110000 TC | 110000 TC 12 months water at 37° C. |
| Rocatec (tribo-chemical Silicate) | 15.8 | 14.3 | 12.3 | 10.5 | 10.0 |
| DE 298 21 398 (tribo-chemical TiO₂) | 15.8 | 13.7 | 12.4 | 9.3 | 8.5 |
| Invention | 18.7 | 18.3 | 15.5 | 14.1 | 13.8 |

TABLE 4

Invention combined with different dental alloys and facing plastic CompoPlus ® (acrylate-based)

| | Shear strength (MPa) | | | |
|---|---|---|---|---|
| Example | initial | 30000 TC | 70000 TC | 110000 TC |
| Degunorm ® | 12.8 | 16.1 | 13.4 | 13.0 |
| Stabilor ® NF IV | 14.6 | 17.9 | 15.4 | 15.6 |
| Palliag ® M | 14.0 | 13.9 | 13.6 | 13.0 |
| Pallatop ® | 18.7 | 18.3 | 15.5 | 14.1 |
| Degupal ® G | 13.9 | 13.7 | 12.6 | 11.5 |
| Biosil ® 1 | 14.3 | 17.3 | 17.4 | 14.6 |

The results in tables 1 to 3 show that with all the systems initial, that is without any thermal cycling and water-storage, good to advantageous adhesive bond values are obtained. After thermal cycling and water-storage a large decrease in adhesive bond properties is observed in the case of the bonding systems and methods according to the prior art, wherein sometimes only a half to a third of the initial values are achieved. In the case of bond values of less than 8 MPa, separation would be expected under clinical use and with additional mechanical strain.

In comparison to that, when using TiO₂ coated blasting grit in accordance with the invention, all the alloys generally exhibit (table 4) very good adhesive bond properties even after thermal cycling and water-storage, with also only a slight decrease (tables 1–3) after a large number of temperature changes and long-term water-storage.

Further variations and modifications of the foregoing will be apparent to those skilled in the art and are intended to be encompassed by the claims appended hereto.

German priority application 100 29 598.3 is relied on and incorporated herein by reference.

We claim:
1. A process for preparing grit blasting particles coated with titanium dioxide comprising sinter-fusing titanium dioxide on the surface of grit blasting particles made of a base material, by continuously passing a mixture of finely divided titanium dioxide and grit blasting particles through a flame in a flame reactor, in a stream of conveying air, and sinter-fusing titanium dioxide on the surface of the grit blasting particles over an average residence time of 0.1 to 5 seconds in a temperature range from 600 to 1200° C.

2. The process according to claim 1, wherein the mixture is blown at a rate of 1 to 50 m/s, with conveying air, centrally into a ring flame operated with fuel gas.

3. The process according to claim 1, wherein the grit blasting particles consist of a ceramic material, glass or metal as the base material.

4. The process according to claim 2, wherein the grit blasting particles consist of a ceramic material, glass or metal as the base material.

5. The process according to claim 1, wherein the grit blasting particles consist of aluminum oxide as the base material.

6. The process according to claim 2, wherein the grit blasting particles consist of aluminum oxide as the base material.

7. The process according to claim 3, wherein the grit blasting particles consist of aluminum oxide as the base material.

8. The process according to claim 1, wherein the grit blasting particles are substantially spherical in shape or have an irregular, angular or rough-edged shape.

9. The process according to claim 2, wherein the grit blasting particles are substantially spherical in shape or have an irregular, angular or rough-edged shape.

10. The process according to claim 3, wherein the grit blasting particles are substantially spherical in shape or have an irregular, angular or rough-edged shape.

11. The process according to claim 4, wherein the grit blasting particles are substantially spherical in shape or have an irregular, angular or rough-edged shape.

12. The process according to claims 1, wherein the particle diameter of the grit blasting particles is in the range 1 $\mu$m to 500 $\mu$m.

13. The process according to claims 1, wherein the particle diameter of the grit blasting particles is in the range 20 $\mu$m to 250 $\mu$m.

14. The process according to claim 1, wherein the titanium dioxide has particle sizes in the range 0.001 $\mu$M to 10 $\mu$M.

15. The process according to claim 1, wherein the titanium dioxide has particle sizes in the range 0.01 $\mu$m to 0.1 $\mu$m.

16. The process according to claim 1, wherein a mixture of 0.1 to 30 wt.%, of titanium dioxide and 70 to 99.9 wt. %, of grit blasting particles is used.

17. The process according to claim 1, wherein a mixture of 1 to 5 wt.%, of titanium dioxide and 95 to 99 wt.%, of grit blasting particles is used.

18. The grit blasting particles coated with titanium dioxide made in accordance with claim 1.

19. The grit blasting particles coated with titanium dioxide made in accordance with claim 2.

20. A process for coating a component selected from the group consisting of metallic, ceramic, metal-ceramic, and composite material with titanium dioxide comprising subjecting said component to grit blasting with grit blasting particles and simultaneously tribochemically coating said component, said grit particles having been made by the process of claim 1.

* * * * *